United States Patent
Ronchi et al.

(10) Patent No.: US 11,331,298 B2
(45) Date of Patent: May 17, 2022

(54) POWDER SOLID DISPERSIONS COMPRISING QUERCETIN, PROCESS FOR THEIR PREPARATION AND FORMULATIONS THEREOF

(71) Applicant: INDENA S.P.A., Milan (IT)

(72) Inventors: Massimo Ronchi, Milan (IT); Elisabetta Frattini, Milan (IT); Antonella Riva, Milan (IT)

(73) Assignee: INDENA S.P.A., Milan (IT)

( * ) Notice: Subject to any disclaimer, the term of this patent is extended or adjusted under 35 U.S.C. 154(b) by 87 days.

(21) Appl. No.: 16/631,285

(22) PCT Filed: Jul. 16, 2018

(86) PCT No.: PCT/EP2018/069284
§ 371 (c)(1),
(2) Date: Jan. 15, 2020

(87) PCT Pub. No.: WO2019/016146
PCT Pub. Date: Jan. 24, 2019

(65) Prior Publication Data
US 2020/0206186 A1    Jul. 2, 2020

(30) Foreign Application Priority Data
Jul. 17, 2017    (EP) .................................... 17181634

(51) Int. Cl.
| | |
|---|---|
| *A61K 31/352* | (2006.01) |
| *A61K 9/10* | (2006.01) |
| *A61K 9/14* | (2006.01) |
| *A61K 9/16* | (2006.01) |
| *A61K 47/24* | (2006.01) |

(52) U.S. Cl.
CPC .............. *A61K 31/352* (2013.01); *A61K 9/10* (2013.01); *A61K 9/145* (2013.01); *A61K 9/1623* (2013.01); *A61K 9/1652* (2013.01); *A61K 47/24* (2013.01)

(58) Field of Classification Search
CPC .......... A61K 31/52; A61K 9/10; A61K 9/145; A61K 9/1623; A61K 9/1652; A61K 9/146; A61K 9/2009; A61K 9/2018; A61K 9/0095; A61K 9/4825; A61K 9/205; A61K 31/352
See application file for complete search history.

(56) References Cited

FOREIGN PATENT DOCUMENTS

| CN | 1 813 677 | | 8/2006 |
|---|---|---|---|
| CN | 1813677 A | * | 8/2006 |

(Continued)

OTHER PUBLICATIONS

Azuma et al., "Enhancing Effect of Lipids and Emilsifiers on the Accumulaton of Quercetin Metabolites in Blood Plasma After the Short-Term Ingestion of Onion by Rats", Biosci. Biotechnol. Biochem., 67 (12) 2548-2555, 2003.

(Continued)

*Primary Examiner* — Carlos A Azpuru
(74) *Attorney, Agent, or Firm* — Nixon & Vanderhye

(57) ABSTRACT

Disclosed are powder solid dispersions including quercetin, phospholipids and a very to freely water soluble carrier. Also disclosed are a process for the preparation of the powder solid dispersions and pharmaceutical, nutraceutical and cosmetic compositions including the solid dispersions.

19 Claims, 1 Drawing Sheet

(56) References Cited

FOREIGN PATENT DOCUMENTS

| CN | 101 904 821 | 12/2010 |
|---|---|---|
| CN | 102580111 | 7/2012 |

OTHER PUBLICATIONS

Gao et al., "Formulation Optimization and In Situ Absorption in Rat Intestinal Tract of Quercetin-Loaded Microemulsion", Colloids and Surfaces B: Biointerfaces 71 (2009) 306-314.

Patel et al., Quercetin Loaded Biopolymeric Colloidal Particles Prepared by Similtaneous Precipitations of Quercetin With Hydrophobic Protein in Aqueous Medium, Food Chemistry 133 (2012) 423-429.

Aytac et al., "Quercetin/B-Cylodextrin Inclusion Complex Embedded Nanofibres: Slow Release and High Solubility", Food chemistry 197 (2016) 864-871.

Nishijima et al., "Chronic Ingestion of Apple Pectin Can Enhance the Absorption of Quercetin", J. Agric. Food Chem. 2009, 57, 2583-2587, Journal of Agricultural and Food Chemistry.

Li et al., "Enhancement of Gastrointestinal Absorption of Quercetin by Solid Liipid Nanoparticles", Journal of Controlled Release 133 (2009) 238-244.

Tamura et al., "Effect of Pectin Enhancement on Plasma Quercetin and Fecal Flora in Rutin-Supplemented Mice"., S648 Journal of Food Science vol. 72, Nr. 9, 2007.

International Search Report, PCT/EP2018/069284, dated Oct. 10, 2018.

Hong-Bo Yang et al: "Preparation and Characterization of the Solid Dispersion Quercetin with Phospholipid". 2017 Joint International Conference on Materials Science and Engineering Application, Apr. 2017 (Apr. 2017), pp. 1-7, XP055438513, Retrieved from the Internet: URL:http://dpi-proceedings.com/index.php/dtmse/article/download/10815/10368 [retrieved on Jan. 5, 2018] the whole document.

Sang Hyun Park et al: "Preparation and Characterization of Quercetin-Loaded Solid Dispersion by Solvent Evaporation and Freeze-Drying Method", Mass Spectrometry Letters, vol. 7, No. 3, Sep. 30, 2016 (Sep. 30, 2016). pp. 79-83. XP055438544, ISSN: 2233-4203. DOI:10.5478/MSL.2016.7.3.79 the whole document.

Written Opinion, PCT/EP2018/069284, dated Oct. 10, 2018.

* cited by examiner

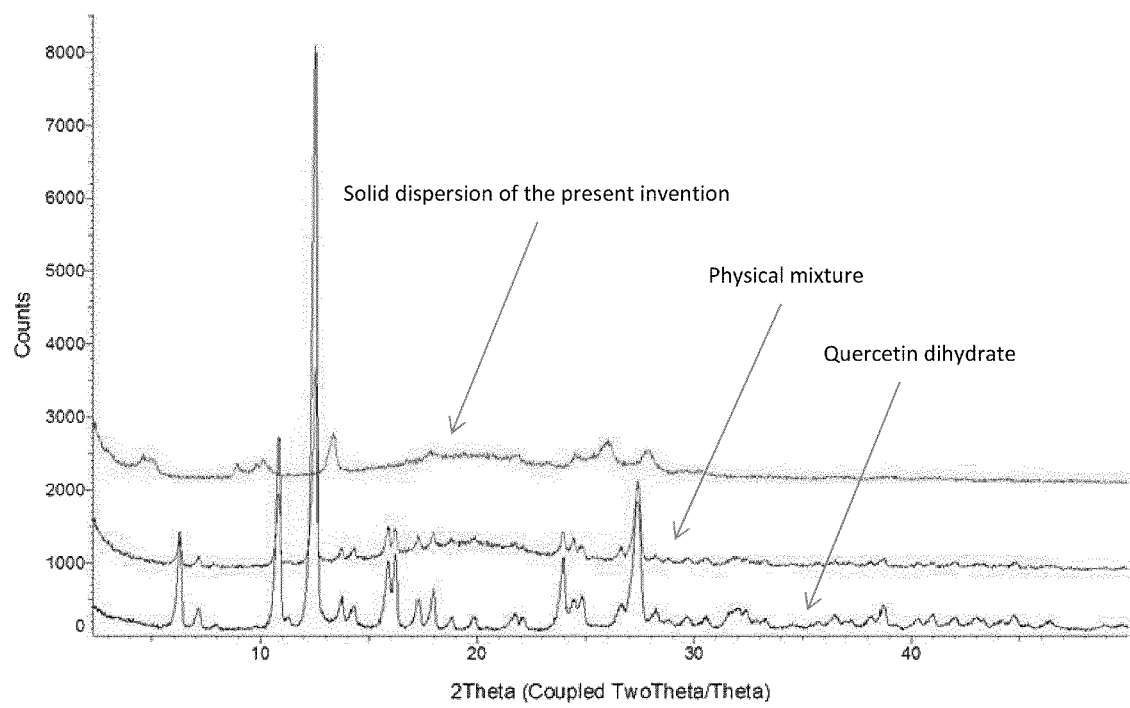

POWDER SOLID DISPERSIONS COMPRISING QUERCETIN, PROCESS FOR THEIR PREPARATION AND FORMULATIONS THEREOF

FIELD OF THE INVENTION

The present invention relates to powder solid dispersions comprising, phospholipids and a very to freely water soluble carrier. The invention also relates to a process for the preparation of said powder solid dispersions and pharmaceutical, nutraceutical and cosmetic compositions comprising said powder solid dispersions.

BACKGROUND OF THE INVENTION

Quercetin (namely 2-(3,4-Dihydroxyphenyl)-3,5,7-trihydroxy-4H-chromen-4-one) having formula (I), belongs to the chemical family of flavonols, a sub-class of flavonoids. Quercetin is a lipophilic citron yellow powder, substantially insoluble in water, but soluble in ethanol, methanol, acetone and other lipophilic organic solvents. Quercetin has a melting point of 316° C.

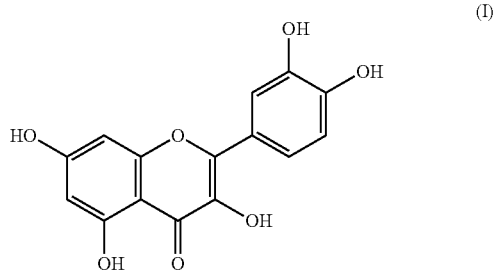 [SMILES: O=c1c(O)c(-c2ccc(O)c(O)c2)oc2cc(O)cc(O)c12]

(I)

Quercetin is present, mainly as quercetin glycosides, in many fruits and vegetables, including apples, grapes, onions, capers, berries, radish.

Quercetin has many potential beneficial effects on human health, including antioxidant, anti-inflammatory, anti-allergy and anti-asthmatic effects. The anti-allergy and anti-asthmatic activities of quercetin are mediated by an inhibitory effect on histamine release by mast cell and basophils. Quercetin has been also studied for its potential anticancer effect due to different mechanisms of action.

As a consequence of these potential beneficial effects on human health, quercetin has gained growing attention as nutraceutical and pharmaceutical ingredient. However, the potential efficacy of quercetin is limited by its low and variable bioavailability which is mainly due to its very poor water solubility. Due to the low and variable oral bioavailability, high unitary doses of quercetin are required to guarantee its pharmacological activity.

The high variability of quercetin in-vivo absorption is substantiated by many studies on animals, which have shown that different dietary factors can strongly influence quercetin absorption (Nishijima, T. et al. (2009). *Journal of agricultural and food chemistry*, 57(6), 2583-2587; Tamura, M. et al. (2007). *Journal of food science*, 72(9); Azuma, K. et al. (2003). Different approaches have been applied to improve quercetin absorption, including incorporation in micro and nano-emulsions (Gao, Y. et al. (2009). *Colloids and Surfaces B: Biointerfaces*, 71(2), 306-314), solid lipid nanoparticles (Li, H., et al. (2009). *Journal of Controlled Release*, 133(3), 238-244), inclusion complexes of cyclodextrins (Aytac, Z., et al. (2016). *Food chemistry*, 197, 864-871), polymer nanoparticles (Patel, A. R., et al. (2012). *Food Chemistry*, 133(2), 423-429), but most of these approaches have many disadvantages including low encapsulation loading, complexity of manufacturing, lack of cost-effective industrial-scale production methods. Moreover most of these approaches have been applied only on laboratory scale and the potential improvement of quercetin oral bioavailability has been demonstrated only in-vitro or in-vivo animal studies.

CN 1 813 677 A (UNIV SICHUAN [CN], published on Aug. 9, 2006, relates to a quercetin liposome injection powder and its preparation method. The liposome powder is made of quercetin, polyglycol-phosphatidylethanolamine, lecithin, cholesterol and an excipient (such as sorbitol, mannitol, glucose, cane sugar or trehalose) and is prepared through a process comprising dissolution of quercetin, polyglycol-phosphatidylethanolamine, lecithin and cholesterol in chloroform and methanol, evaporation of the solvents to obtain a dry residue, addition of a sterile broth and an excipient to obtain a water solution which is subjected to ultra-sonic treatment and lyophilization to obtain a powder.

CN 102580111B (UNIV SICHUAN), published on Apr. 9, 2014, discloses a liposome which comprises quercetin entrapped in a cyclodextrin. Specifically, the liposome is prepared through a process comprising the addition of quercetin to a solution of hydroxypropyl-beta-cyclodextrin in a solvent selected from one or more of anhydrous alcohol, n-butyl alcohol and ether to obtain a solution; the addition of egg yolk lecithin or soybean phospholipid, cholesterol, polyethylene glycol-distearyl acid, phosphatidylethanolamine to the solution, followed by addition of the resulting solution to a water solution of sucrose and removal of the solvent by lyophilization. In the liposome, lecithin or soy phospholipids are used in excess with respect to quercetin; in greater detail, the weight ratio between quercetin and lecithin or soy phospholipid is from 1:5 to 1:50.

CN 101 904 821 A (LINGMIN JIANG; LEI GAO), published on Dec. 8, 2010 relates to a quercetin nano lyophilized powder having a mean diameter of less than 300 nm, preferably from 100 to 300 nm, and consisting of quercetin, a surfactant and a freeze drying protectant. The surfactant can be, inter alia, a phospholipid or soy lecithin, and the freeze drying protectant is a polysaccharide or a polyol. The quercetin powder is manufactured through a process carried out entirely in water; specifically, a surfactant is dispersed in water, then quercetin is added and the resulting suspension is homogenized under pressure and lyophilized. The freeze drying protectant can be added to the surfactant dispersion before addition of quercetin or before lyophilization.

All of CN 1 813 677 A, CN 102580111B and CN 101 904 821 A disclose liposomes, whose preparation includes the use of water.

Hong-Bo Yang, et al. (2017) *Joint International Conference on Materials Science and Engineering Application*, April 2017, pages 1-7) disclose the preparation of a solid dispersion of quercetin in a phospholipid by dissolution of quercetin and a phospholipid at a 1:2 weight ratio in tetrahydrofuran, stirring, filtration and drying under vacuum at 50° C. While X-rays suggest that quercetin as such is a crystalline solid, X-ray analysis of the solid dispersion show that in the solid dispersion quercetin is present in an amorphous form.

Sang Hyun Park et al. *Mass Spectrometry Letters*, vol. 7, no. 3, 30 Sep. 2016, pages 79-83) teach to prepare a solid dispersion of quercetin by dissolution of quercetin, a hydrophilic polymer and a carrier in ethyl alcohol, followed by evaporation to provide a residue which is taken up in HPMG, PEG 8000, PVP K40 and water, to provide a clear solution which is subjected to lyophilization to provide the solid dispersion. This document states that quercetin is thus transformed from a crystalline to an amorphous form.

Due to the poor and variable absorption of quercetin there is still the need to develop delivery systems able to promote its oral bioavailability and to guarantee a more constant absorption into the systemic circulation and pharmacological activity accordingly.

DESCRIPTION OF THE FIGURE

FIGURE: X-ray diffraction pattern of a solid dispersion of the invention (quercetin:phospholipids:carrier weight ratio=3:3:2), quercetin dihydrate and a physical mixture of quercetin dihydrate (quercetin:phospholipids:carrier weight ratio=3:3:2),

SUMMARY OF THE INVENTION

The present invention relates to a powder solid dispersion comprising quercetin, phospholipids and a carrier very soluble to freely soluble in water.

The invention also concerns a process for preparing the powder solid dispersion comprising dissolving or suspending in an anhydrous organic solvent and under heating quercetin, phospho lipids and a water-soluble carrier and then removing the solvent to obtain the powder solid dispersion.

Further object of the invention are formulations for oral administration comprising the powder solid dispersion and one or more pharmaceutically and food acceptable excipients.

DESCRIPTION OF THE INVENTION

It has been surprisingly found that powder solid dispersions comprising, preferably consisting of, quercetin, phospholipids and a carrier very soluble to freely soluble in water are characterized by an improved solubility and oral bioavailability of quercetin in humans.

According to a preferred embodiment, quercetin is quercetin dihydrate.

The phospholipids may be selected from the group consisting of lecithins from soy, sunflower or egg, phosphatidyl choline, phosphatidyl serine, phosphatidyl ethanolamine, or their mixtures, wherein the acyl groups, which may be the same or different, are mostly derived from palmitic, stearic, oleic, linoleic, linolenic acids. In a preferred embodiment, the lecithin is soy or sunflower lecithin; in a more preferred embodiment, the lecithin is sunflower lecithin.

The quercetin to phospholipids weight ratio may range from 5:1 to 1:1, preferably from 2:1 to 1:1.

According to the invention, the term "very soluble" and the term "freely soluble" have the meaning, as defined in the European Pharmacopeia 5.0, reported in the following scheme:

| Scheme | |
|---|---|
| Descriptive term | Approximate volume of solvent in milliliters per gram of solute |
| Very soluble | less than 1 |
| Freely soluble | from 1 to 10 |

The terms used have the defined significance referred to a temperature between 15° C. and 25° C.

The term "carrier" is used hereinafter to indicate "a carrier very soluble to freely soluble in water". The carrier may be selected from the group consisting of mono- and di-saccharides (such as sucrose, fructose, maltodextrins); polyalcohols (such as mannitol, sorbitol, xylitol); soluble oligo- and poly-saccharides (such as dextran, pullulan). In a preferred embodiment, the carrier is a maltodextrin.

The quercetin to carrier weight ratio may range from 1:5 to 5:1, preferably from 1:2 to 3:1. For the avoidance of doubt, throughout the present application, when ranges are indicated, range ends are included.

Preferably, the solid dispersion of the invention has an average particle size distribution ranging from 100 μm to 300 μm.

Preferably, the solid dispersion of the invention consists only of quercetin, phospholipids and a carrier as defined above. In a preferred embodiment, the solid dispersion of the invention consists of quercetin, sunflower lecithin and maltodextrin; in another preferred embodiment, the solid dispersion of the invention consists of quercetin, sunflower lecithin and fructose.

Without being bound to theory, it is believed that the carrier plays a fundamental role for the performance of the powder solid dispersion, promoting the fast dissolution rate of quercetin and contributing to promote its oral bioavailability. It is also believed that the soluble carrier also plays a relevant role in optimizing the physical properties of the final product.

It has been found that in the solid dispersions of the invention the physicochemical properties of quercetin are significantly modified, so much so that quercetin's pharmacological performances are improved even if the quercetin/phospholipids weight ratio is low. Surprisingly, it has been observed that quercetin, in particular quercetin dihydrate, can be incorporated in the phospholipids in high amount and that dissolution in water is fast even though X-rays of the solid dispersions of the invention show that a significant amount of crystalline is still present. Indeed, on the basis of the teaching of the aforementioned publications of Hong-Bo Yang, ET AL and of Sang Hyun Park ET AL one would expect that fast dissolution would be due to absence of quercetin in the crystalline form.

The solid dispersions of the invention can be advantageously prepared with a process (or method) which avoids the use of chlorinated solvents and does not comprise any lyophilization steps and which can be easily scaled-up on pilot and industrial equipment.

Therefore, a further object of the invention is a process for preparing a powder solid dispersion according to the present invention comprising dissolving or suspending in an organic solvent comprising less than 5% wt water and under heating quercetin, phospho lipids and a water-soluble carrier and then removing the solvent to obtain the powder solid dispersion.

In one embodiment, the process comprises the following steps:

a) preparing a solution of quercetin in an organic, solvent [solution (S1)];

b) preparing a solution/suspension of phospholipids in the same solvent used in step a) [solution or suspension (S2)];

c) contacting the solution of quercetin obtained in step a) with the solution/suspension of phospholipids obtained in step b) to provide a further solution or suspension [suspension or solution (S3)];

d) adding a carrier very soluble to freely soluble in water carrier to the solution or suspension obtained in step c) and e) removing the solvent under vacuum or under spray-drying, to form a powder solid dispersion.

In another embodiment, the process comprises the following steps:

a-1) preparing a solution of quercetin in an organic solvent comprising less than 5% wt water[solution (S1)];

b-1) adding phospholipids and a carrier very soluble to freely soluble in water carrier to solution (S1) to provide a solution or suspension of quercetin, phospholipids and carrier in the solvent [solution or suspension (S3)] and c-1) removing the solvent under vacuum or under spray-drying to form a powder solid dispersion.

The organic solvent is a food grade solvent having a boiling point at atmospheric pressure not higher than 80° C.; preferably, the solvent is a $C_1$-$C_4$ straight or branched alcohol, ethyl acetate or acetone, More preferably, the solvent is selected form the group comprising ethyl alcohol, isopropyl alcohol, n-propyl alcohol, n-butanol, ethyl acetate, acetone. Even more preferably, the solvent is selected from ethanol and ethyl acetate.

The process of the invention is carried out using solvents containing less than 5% wt of water and it does not comprise any steps of dissolution in water.

The dissolution or suspension of quercetin, phospholipids and carrier is carried out under heating; in particular, steps a) to d) and a-1) and b-1) of the preferred embodiments are carried out under heating; typically, heating is carried out at a temperature ranging from 30° C. to the solvent boiling temperature, preferably from 40° C. to 80° C., more preferably from 50° C. to 60° C., until partial or complete dissolution or suspension of quercetin, phospholipids and carrier. A person skilled in the art shall be able to determine the time necessary to obtain complete or partial solubilization (i.e. suspension) of quercetin, phospho lipids and carrier.

For the avoidance of doubt, within the present application, the term "solution" denotes a liquid composition which, upon visual inspection, is clear at the selected temperature; the term, "suspension" denotes a liquid composition which, upon visual inspection, is opaque but nonetheless homogeneous.

After steps e) or c1), the powder solid dispersion may be calibrated, to obtain the desired particle size distribution within the aforementioned range of 100 µm to 300 µm and may be eventually mixed with pharmaceutically and food acceptable excipients, such as silicon dioxide, talc, magnesium stearate, to further improve its physical and technological properties.

The fast dissolution of the very to freely water soluble carrier, on which the quercetin and phospholipids are loaded, contributes to enhance quercetin wettability and fast dissolution. As a consequence, a high quercetin concentration in the absorption site is created, determining a high concentration gradient which is the driving force for the passive diffusion of quercetin through the absorption membranes of the gastro-intestinal tract.

Without being bound to theory, it is believed that the complete or at least partial co-solubilization of quercetin and phospho lipids in the selected organic solvent during the process of the invention contributes to improve quercetin's solubility and oral bioavailability.

A calorimetric analysis by Differential Scanning calorimetry (DSC) was performed to determine, on the basis of the reduction of the enthalpy of fusion (J/g), the degree of amorphization of quercetin in the powder solid dispersion compared to the totally crystalline unformulated quercetin, in particular compared to quercetin dihydrate. X-ray analysis was also performed. The X-ray diffraction pattern of the powder solid dispersions of the invention showed characteristic peaks at 8.9±0.2, 13.5±0.2, 26.0±0.2 and 27.8±0.2 2θ angle (CuKα λ=1.5419 Å)

Therefore, a further object of the invention is a powder solid dispersion comprising, preferably consisting of, quercetin, phospholipids and a carrier very soluble to freely soluble in water wherein the quercetin to phospholipids weight ratio ranges from 5:1 to 1:1 and characterized by an X-ray diffraction pattern characteristic peaks at 8.9±0.2, 13.5±0.2, 26.0±0.2 and 27.8±0.2 2θ angle (CuKα λ=1.5419 Å). For the avoidance of doubt, all preferred definitions and embodiment concerning quercetin, phospholipids, the carrier, weigh ratio and particle size apply to this object of the invention.

The powder solid dispersion of the invention is easy to incorporate in conventional solid dosage forms, like tablets and capsules, but also in ready-to-use or extemporary liquid formulations, that are particularly useful and appealing in the sport nutrition sector, which represents one of the most important field of application of quercetin.

Another object of the invention are formulations for oral administration containing the powder solid dispersions of the invention and one or more pharmaceutically and food acceptable excipients, such as disintegrants, lubricants, binders, coating agents, colorants, absorption promoters, solubilizing agents, stabilizers, flavors, sweeteners, antiseptics, preservatives, antioxidants and the like.

The formulations according to the invention may be prepared according to conventional techniques as described for example in Remington's Pharmaceutical Handbook, Mack Publishing Co., NY USA.

Examples of dosage forms of the formulations of the invention include coated or uncoated tablets, chewable tablets, capsules, soft gelatin capsules, hard gelatin capsules, caplets, lozenges, chewable lozenges, extemporary and ready-to-use liquid formulation and combinations thereof.

The improved solubility of quercetin contained in the powder solid dispersion of the invention was evaluated in simulated gastric and intestinal fluids.

The oral bio availability of the powder solid dispersions of quercetin was evaluated in humans compared to (unformulated, in free form) quercetin. The results show a significant improvement of oral bioavailability of quercetin in a powder solid dispersion according to the invention compared to (unformulated, in free form) quercetin dihydrate.

A pharmacokinetic study on human subjects confirmed the improvement of oral bioavailability of about 50-times for quercetin of the powder solid dispersions of the invention in comparison with quercetin as such.

The obtained powder solid dispersions of the invention are characterized by a high content of quercetin, by an improvement of quercetin solubility and dissolution rate, by an improvement of the oral bioavailability of quercetin in humans (AUC and $C_{max}$), if compared to the quercetin as such. All this is surprising; indeed, while the DSC analysis of the powder solidi dispersions of the invention seemed to indicate an almost quantitative amorphization of quercetin, which was thought to be necessary to increase solubilization in body fluids and bioavailability, the X-ray analysis showed significant peaks of quercetin in a crystalline form different from the dihydrate form.

The following examples further describe the invention.

EXAMPLES

Example 1: Preparation of a Powder Solid Dispersion 375 g of quercetin dihydrate are added to 13 L of ethyl alcohol, then heating at 60° C. and mixing for about 15 minutes until complete dissolution.

375 g of sunflower lecithin and 250 g of maltodextrin are added to the quercetin solution. The obtained suspension is stirred at 50° C. for about 60 minutes. The solvent is removed under reduced pressure until a soft mass is obtained. The remaining solvent is removed under vacuum at 50° C. for about 12 hours, up to a ethyl alcohol residue lower than 10000 ppm.

Example 2: Preparation of a Powder Solid Dispersion 350 g of quercetin dihydrate to 12 L of ethyl acetate is added, then heating at 60° C. and mixing for about 15 minutes until complete dissolution.

300 g of sunflower lecithin and 350 g of fine fructose are added to the quercetin solution. The obtained suspension is stirred at 50° C. for about 60 minutes. The solvent is removed under reduced pressure until a soft mass is obtained. The remaining solvent is removed under vacuum at 50° C. for about 16 hours, up to a ethyl acetate reside lower than 5000 ppm.

Example 3: Characterization of the Powder Solid Dispersion by DSC (Differential Scanning Calorimetry) and by X-Ray Analysis The powder solid dispersion obtained in Example 1 was analyzed by DSC compared to (unformulated, in free form) quercetin dihydrate. The analysis was performed using a Mettler DSC1 System. Heat flow was recorded from 30 to 300° C. with linear heating rate (10° C./min), using closed aluminum crucibles (40 µl volume) with a pinhole, under a 50 ml/min nitrogen flow. About 5-10 mg of powder were used for each measurement. The thermal profiles were acquired and elaborated by a dedicate software. The disappearance of the endothermic peak of quercetin in the solid dispersion DSC curve seemed to indicate almost quantitative amorphization. Instead, the XRDP (X-Ray Diffraction Pattern) of the powder solid dispersion obtained in Example 1 compared to that of quercetin dihydrate and of a physical mixture having the same quali-quantitative composition of the solid dispersion obtained in Example 1 (Physical Mixture) (see FIGURE) showed that the solid dispersion of the invention still contains a significant amount of crystalline form that is, however, different from quercetin dihydrate as such or from quercetin dihydrate present in the physical mixture.

The XRDP of quercetin dihydrate of this example is characterized by the most intense diffraction peak at 12.5 2θ angle with relative intensity of 100% (net intensity 7096 counts). In the physical mixture the same peak at 12.5 2θ angle remains the most intense (relative intensity 100%, net intensity 2577 counts), while in the solid dispersion at 12.5 2θ angle only noise baseline is detectable.

On the contrary, in the XRDP of the solid dispersion of this example the most intense diffraction peak is at 13.5 2θ angle with relative intensity of 100% (net intensity 501 counts) while both in quercetin dihydrate and in the physical mixture XRDPs, at 13.5 2θ only noise baseline is detectable.

As far as crystallinity is concerned, according to Bruker software Diffrac EVA v. 3.1 and its algorithm "Crystallinity" the degree of crystallinity calculated from the XRDP for the three materials of the example are: quercetin dihydrate=85%; physical mixture=47%; solid dispersion=37%.

Example 4: Characterization of the Powder Solid Dispersion—Solubility Studies in Simulated Gastro-Intestinal Fluids Quercetin dihydrate, quercetin powder solid dispersion obtained in Example 1 and a mechanical (physical) mixture of the component of the said solid dispersion were subjected to comparative solubility experiments, in the presence of high excess of analyte, using the following simulated gastro-intestinal fluids:

fasted state simulated gastric fluid;
fasted state simulated intestinal fluid;
fed state simulated intestinal fluid.

Equivalent amounts of quercetin were used during the experiments. Quercetin dihydrate, quercetin powder solid dispersion of Example 1 and the mechanical (physical) mixture were kept under magnetic stirring for 2 hours. The supernatant was filtered and the quercetin concentration was calculated by HPLC analysis. The results of these solubility studies are reported in the following table 1:

TABLE 1

| Material | Quercetin (µg/mL) |
|---|---|
| Fasted state simulated gastric fluid (pH 1.6) | |
| Quercetin powder solid dispersion (Example 1) | 8.2 |
| Mechanical mixture | 0.1 |
| Quercetin dihydrate | <LOD |
| Fasted state simulated intestinal fluid (pH 6.5) | |
| Quercetin powder solid dispersion (Example 1) | 83.8 |
| Mechanical mixture | 19.9 |
| Quercetin dihydrate | 7.5 |
| Fed state simulated intestinal fluid (pH 5.0) | |
| Quercetin powder solid dispersion (Example 1) | 216.6 |
| Mechanical mixture | 29.1 |
| Quercetin dihydrate | 19.1 |

The results of the solubility studies show that, despite the presence of a significant amount of quercetin in crystalline form, the powder solid dispersion of the invention is much more soluble than quercetin dihydrate as such or as a mechanical mixture with phospho lipids.

Example 5: Pharmacokinetic Study on Humans

A single dose randomized, crossover pharmacokinetic study in healthy volunteers under fasting conditions was performed using film-coated tablets containing 500 mg of (unformulated) quercetin dihydrate, 500 mg of quercetin (40%) powder solid dispersion (corresponding to 200 mg of quercetin dihydrate) and 250 mg of quercetin (40%) powder solid dispersion (corresponding to 100 mg of quercetin dihydrate). The mean pharmacokinetic parameters ($AUC_{0-\infty}$; $C_{max}$) are reported in the following table 2:

TABLE 2

| Pharmacokinetic parameters | Quercetin dihydrate 500 mg tablets | Quercetin solid dispersion 500 mg tablets | Quercetin solid dispersion 250 mg tablets |
| --- | --- | --- | --- |
| $AUC_{0-\infty}$ (min * ng/mL) | 5405.0 | 96163.9 | 50747.1 |
| $C_{max}$ (ng/mL) | 10.93 | 223.10 | 126.35 |

The results show that, despite the presence of a significant amount of quercetin in crystalline form, the solid dispersions of the invention have a much more higher AUC and $C_{max}$ than quercetin dihydrate as such.

Example 6: Formulation Containing Quercetin Powder Solid Dispersion (Film-Coated Tablets)

| Quali-quantitative composition | (mg/tablets) |
| --- | --- |
| Quercetin solid dispersion (Example 1) | 250.0 mg |
| Dicalcium phosphate dihydrate | 270.0 mg |
| Mannitol | 180.0 mg |
| Sodium croscarmellose | 40.0 mg |
| Silicon dioxide | 15.0 mg |
| Talc | 15.0 mg |
| Magnesium stearate | 10.0 mg |
| Film-coating | 20.0 mg |

Example 7: Formulation Containing Quercetin Powder Solid Dispersion (Soft Gelatin Capsules)

| Quali-quantitative composition | (mg/capsule) |
| --- | --- |
| Quercetin solid dispersion (Example 2) | 300.0 mg |
| Flaxseed oil | 345.0 mg |
| Beeswax | 10.0 mg |
| Fluid lecithin | 5.0 mg |

Example 8: Formulation Containing Quercetin Powder Solid Dispersion (Granules for Dispersion)

| Quali-quantitative composition | (mg/tablets) |
| --- | --- |
| Quercetin solid dispersion (Example 1) | 500.0 mg |
| Maltodextrin | 2330.0 mg |
| Guar gum | 300.0 mg |
| Flavours | 200.0 mg |
| Citric acid | 155.0 mg |
| Sucralose | 15.0 mg |

The invention claimed is:

1. A powder solid dispersion comprising quercetin, phospholipids and a carrier very soluble to freely soluble in water, wherein the quercetin to phospholipids weight ratio ranges from 5:1 to 1:1, and
wherein the quercetin to carrier weight ratio ranges from 1:5 to 5:1.

2. The powder solid dispersion according to claim 1, wherein quercetin is quercetin dihydrate.

3. The powder solid dispersion according to claim 1, wherein the phospholipids are selected from the group consisting of lecithins from soy, sunflower or egg, phosphatidyl choline, phosphatidyl serine, phosphatidyl ethanolamine, or their mixtures, wherein the acyl groups, which are the same or different, are mostly derived from palmitic, stearic, oleic, linoleic, linolenic acids.

4. The powder solid dispersion according to claim 1, wherein the quercetin to phospholipids weight ratio ranges from 2:1 to 1:1.

5. The powder solid dispersion according to claim 1, wherein the carrier is selected from the group consisting of mono- and di-saccharides; polyalcohols; soluble oligo- and poly-saccharides.

6. The powder solid dispersion according to claim 5, wherein the mono- and di-saccharides are selected from the group consisting of sucrose, fructose, maltodextrins.

7. The powder solid dispersion according to claim 5, wherein the polyalcohols are selected from the group consisting of mannitol, sorbitol, xylitol.

8. The powder solid dispersion according to claim 5, wherein the soluble oligo- and poly-saccharides are dextran or pullulan.

9. The powder solid dispersion according to claim 1, wherein the quercetin to carrier weight ratio ranges from 1:2 to 3:1.

10. The powder solid dispersion according to claim 1 and having an average particle size distribution ranging from 100 μm to 300 μm.

11. The powder solid dispersion according to claim 1, having an X-ray diffraction pattern having peaks at 8.9±0.2, 13.5±0.2, 26.0±0.2 and 27.8±0.2 2θ angle (CuKαλ=1.5419 Å).

12. A process for preparing a powder solid dispersion according to claim 1, comprising dissolving or suspending in a suitable anhydrous organic solvent and under heating quercetin, phospholipids and a water-soluble carrier and then removing the solvent to obtain a powder solid dispersion wherein the quercetin to phospholipids weight ratio ranges from 5:1 to 1:1, and wherein the quercetin to carrier weight ratio ranges from 1:5 to 5:1.

13. The process according to claim 12 which comprises the following steps:
    a) preparing a solution of quercetin in an organic solvent comprising less than 5% wt water;
    b) preparing a solution/suspension of phospholipids in the same solvent used in step a);
    c) reacting a solution of quercetin obtained in step a) with a solution/suspension of phospholipids obtained in step b);
    d) adding a carrier very soluble to freely soluble in water to the mixture obtained in step c) and
    e) removing the solvent under vacuum or under spray-drying to form a powder solid dispersion.

14. The process according to claim 12 which comprises the following steps:
    a-1) preparing a solution (S1) of quercetin in an organic solvent comprising less than 5% wt. water;
    b-1) adding phospholipids and a carrier very soluble to freely soluble in water carrier to said solution (S1) to provide a solution or suspension (S3) of quercetin, phospholipids and carrier in the solvent and
    c-1) removing the solvent under vacuum or under spray-drying to form a powder solid dispersion.

15. The process according to claim 11, wherein the organic solvent is selected form the group consisting of ethyl alcohol, isopropyl alcohol, n-propyl alcohol, n-butanol, ethyl acetate, acetone.

16. The process according to claim 13 wherein steps a) to d) are carried out at a temperature ranging from 40° C. to 80° C.

17. The process according to claim 14 wherein steps a1) and b1) are carried out at a temperature ranging from 40° C. to 80° C.

18. Formulation for oral administration comprising a powder solid dispersion according to claim 1 and one or more pharmaceutically and food acceptable excipients.

19. The powder solid dispersion according to claim 2, wherein the phospholipids are selected from the group consisting of lecithins from soy, sunflower or egg, phosphatidyl choline, phosphatidyl serine, phosphatidyl ethanolamine, or their mixtures, wherein the acyl groups, which are the same or different, are mostly derived from palmitic, stearic, oleic, linoleic, linolenic acids.

* * * * *